(12) United States Patent
Newkirk

(10) Patent No.: US 6,197,596 B1
(45) Date of Patent: Mar. 6, 2001

(54) MONITORING AND/OR PROGNOSTIC OF ANTIBODY-MEDIATED AUTOIMMUNE DISEASES

(75) Inventor: Marianna M. Newkirk, Pierrefonds (CA)

(73) Assignee: McGill University, Montreal (CA)

( * ) Notice: Subject to any disclaimer, the term of this patent is extended or adjusted under 35 U.S.C. 154(b) by 0 days.

(21) Appl. No.: 09/204,482

(22) Filed: Dec. 3, 1998

(30) Foreign Application Priority Data

Dec. 4, 1997 (CA) .................................................. 2223481

(51) Int. Cl.$^7$ .................................................. G01N 33/564
(52) U.S. Cl. ........................ 436/506; 435/7.2; 530/388.7; 530/389.6; 530/395
(58) Field of Search ................................. 424/145.1, 531, 424/810; 435/2, 7.1, 7.2; 436/506, 811, 536; 530/391.1, 389.1, 389.3, 350, 388.25, 388.7, 389.6, 395

(56) References Cited

PUBLICATIONS

Hogasen, K. et al., *J. Immunol. Meth.* 160:107–115 (1993).
Liang, M.H. et al., *Arthritis Rheum.* 32:1107–1118 (1989).
The Merck Manual. 16$^{th}$ Edition, 1992, pp. 338–342.*
Rosenberg et al. Int. J. Biochem. Cell. Biol. vol. 27: 633–645, 1995.*

Newkirk et al. J. Rheumatology vol. 26: 597–603, 1999.*

Cuida et al. Clin. and. Exp. Rheumatology. vol. 15: 615–623, 1997.*

Witte et al.; Am. J. of Pathol.; vol. 143; No. 3; p. 763–773, 1993.*

Murakami et al.; J. of Biol. Chem. vol. 266; p. 15414–15419, 1991.*

* cited by examiner

*Primary Examiner*—Patrick Nolan
(74) *Attorney, Agent, or Firm*—Nixon Peabody, LLP

(57) ABSTRACT

The present invention relates to a method to determine antibody-mediated autoimmune diseases in a patient, which comprises the steps of: a) determining the amount of clusterin present in a serum, saliva or tissue sample of the patient with an anti-clusterin antibody; b) comparing the amount of clusterin in step a) with normal serum, saliva or tissue sample, wherein a lower than normal amount is indicative of active antibody-mediated autoimmune disease.

2 Claims, 3 Drawing Sheets

MONITORING AND/OR PROGNOSTIC OF ANTIBODY-MEDIATED AUTOIMMUNE DISEASES

BACKGROUND OF THE INVENTION (a) Field of the Invention

The invention relates to the monitoring and/or prognostic of antibody-mediated autoimmune diseases, and treatments thereof.

(b) Description of Prior Art

Systemic lupus erythematosus (SLE) is a disease that predominantly affects women, and is characterized by high levels of circulating autoantibodies, which are thought to play an integral role in its pathogenesis. Most of the autoantibodies are specific for proteins that are normally sequestered inside the cell. Much recent interest has focused on the role that apoptosis plays in the movement of these autoantigens to blebs at the cell surface. We speculate that if this happened every time apoptosis occurred, inflammation would occur throughout the body in individuals with high levels of these circulating autoantibodies. This, however, does not occur in SLE, where the disease is more tissue specific with skin lesions and arthritis the most common features. Less common, but generally associated with morbidity, are the renal complications. We reasoned that there must be another level of control, which leads to the inflammation at the different sites. One protein of interest is clusterin, which is induced by the same stimuli that induce apoptosis, such as TNF, UVB irradiation, and serum deprivation.

Clusterin (also known as apoJ, and complement lysis inhibitor) is a 70–80 kD heterodimeric sulfated glycoprotein that is expressed by a large number of cells, including epithelial, polymorphonuclear and neuronal cells, as well as platelets. It has a protective role, and its expression at sites of tissue remodeling and apoptosis is thought to prevent antibody mediated lysis and inflammation. Clusterin not only binds and inhibits the terminal components of complement, but also binds immunoglobulin, apo-IA, and TGF receptors (both type I and II).

It would be highly desirable to be provided with means to monitor antibody-mediated autoimmune diseases.

SUMMARY OF THE INVENTION

One aim of the present invention is to provide means to monitor antibody-mediated autoimmune diseases.

Another aim of the present invention is to provide treatments of antibody-mediated autoimmune diseases.

In accordance with the present invention there is provided a method to determine antibody-mediated autoimmune diseases in a patient, which comprises the steps of:

a) determining the amount of clusterin present in a serum, saliva or tissue sample of the patient with an anti-clusterin antibody;

b) comparing the amount of clusterin in step a) with normal serum, saliva or tissue sample, wherein a lower than normal amount is indicative of antibody-mediated autoimmune and/or injury-mediated disease.

In accordance with the present invention there is provided a method to monitor antibody-mediated autoimmune diseases in a patient, which comprises measuring the clusterin levels according to the method of the present invention weekly to monthly to follow disease activity, wherein a drop in the clusterin levels is indicative of more active disease which necessitates more aggressive treatment.

In accordance with the present invention there is provided a method for the treatment of antibody-mediated autoimmune diseases in a patient, which comprises administering a pharmaceutically effective amount of an agent which increases clusterin expression.

The agent includes, without limitation, folic acid, tamoxifen and Tripterigium Wilfordii Hook(TWH-f).

For the purpose of the present invention the following terms are defined below.

The expression "antibody-mediated autoimmune diseases" is intended to mean any diseases caused by or related to antibodies present in a patient, including, without limitation, diseases such as dermatomyositis, thyroiditis, systemic lupus erythematosus, Sjogren's syndrome, IgA nephropathy, and others, as well as other injury related diseases where antibodies play a role.

DETAILED DESCRIPTION OF THE INVENTION

Figure 1:
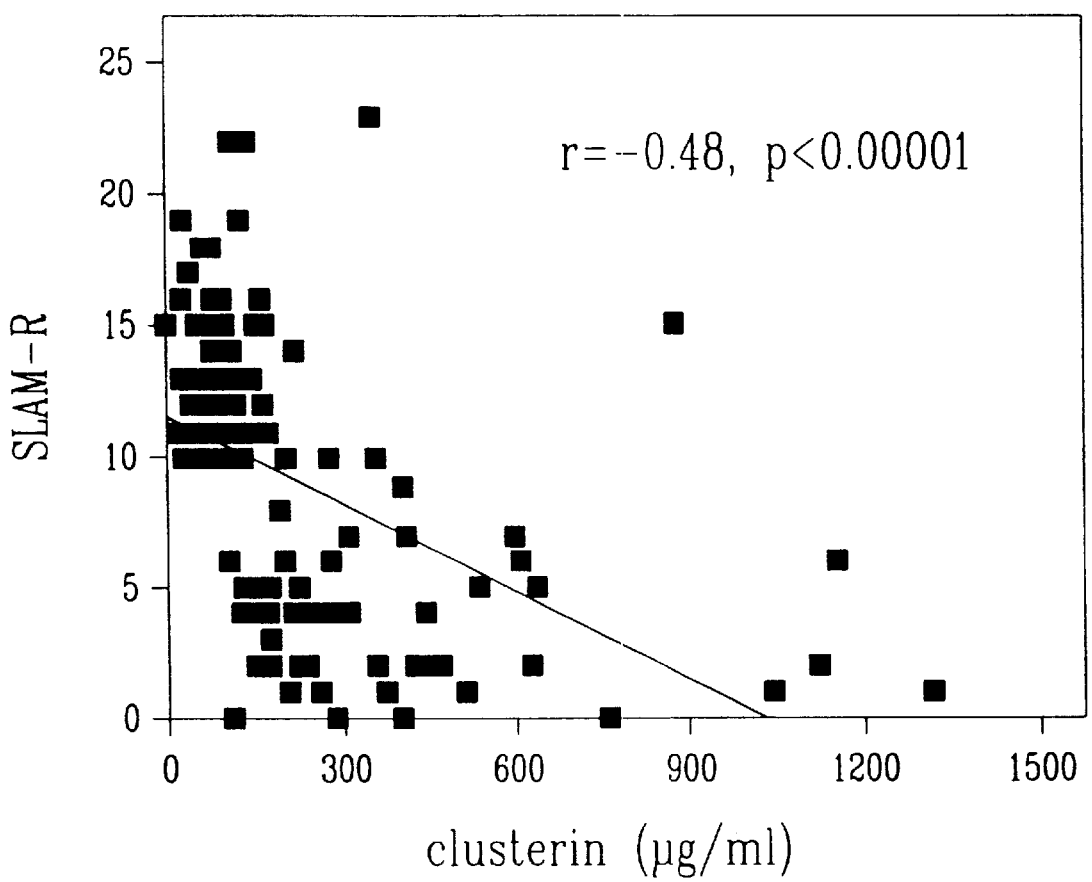
FIG. 1 illustrates serum clusterin levels inversely correlate with systemic lupus activity measure (SLAM-R) in a cohort of 80 patients, with a total of 115 visits.

Patients with systemic lupus erythematosus (SLE) mount an antibody response to a number of different cellular components, most of which are sequestered inside cells. These autoantibodies are thought to play a pathogenic role. The typical skin lesions in patients with SLE can be initiated following exposure to sunlight, indicating that damage to cells can be a trigger. Recent evidence points to apoptosis as a mode of altering the expression of these autoantigens, possibly making them accessible to circulating autoantibodies. Clusterin, an anti-inflammatory protein, which is capable of binding and inactivating complement should theoretically protect against autoantibody mediated inflammation. We have found that serum clusterin levels are significantly decreased in patients with SLE and correlate inversely with disease activity. Low clusterin levels are associated with the skin lesions, loss of hair, proteinuria and the presence of arthritis. The clusterin levels did not correlate with either systemic complement consumption, as measured by C3 or C4, or with prednisone use. It is clear from our study that low levels of clusterin are detrimental to patients with SLE and appear to contribute to the disease pathogenesis.

Measurement of serum clusterin

Serum clusterin was measured by a modified capture ELISA (Hogasen, K. et al., *J. Immunol. Meth.* 160:107–115 (1993)). Clusterin was captured onto high binding ELISA plates (either EIA plus, ICN, Montreal, QC or plate F, Greiner, BellCo, Vineland N.J.) from the purified standard (dilution curve was established using human clusterin, Quidel, San Diego, Calif.) or sera diluted from 1:100 to 1:8000 (most frequent dilution used to calculate amount of clusterin was 1:4000) as appropriate, in PBS, 0.2% Tween™ 20. After an overnight incubation at 4° C., the plates were washed with PBS, 0.1% TWEEN™ 20. Monoclonal anticlusterin antibody (SP40,40/G7 mAB, Quidel) diluted 1:10,000 in PBS, 0.1% Tween™ 20 was added and the plates were incubated for 1 hr at 37° C. After washing, HRP-conjugated F(ab')$_2$ fragments of sheep anti-mouse IgG antibodies (Jackson, BioCan, Mississauga, ON) were used (diluted 1:20,000) to detect the bound anti-clusterin antibodies. After a 1 hr incubation at 37° C., the plate was washed and the substrate added (o-phenylene-diamene) for 30 minutes at 25° C. The reaction was terminated with 4 M H$_2$SO$_4$, and the optical density at 492 (reference 690) was measured, using an ELISA plate reader (SLT LabInstruments, Fisher, Montreal, QC) . Since there is a saturation level to the plates, clusterin was calculated from that dilutions of serum or plasma where with a doubling dilution there was a 2-fold change in O.D.

Systemic lupus erythematosus disease activity score

SLAM-R was measured as previously described (Liang, M. H. et al., *Arthritis Rheum.* 32:1107–1118 (1989))

The SLAM covers symptoms of SLE that occurred during the previous month, and includes 24 clinical manifestations and 8 laboratory parameters to evaluate organs which cannot be assessed otherwise. A manifestation or symptom is determined to be either active or not active. For the complete list of data compiled and used to calculate SLAM see attached.

Statistical methods

For each parameter measured, or for the global disease activity, mean values of clusterin were calculated, along with the S.E.M. (as presented in the text). The 95% confidence intervals are plotted in FIGS. 2–4. The significance of the difference in the means was obtained using non-parametric, 2-tailed analyses (Mann-Whitney U).

Results

We measured the levels of serum clusterin by a capture ELISA (Hogasen, K. et al., *J. Immunol. Meth.* 60:107–115 (1993)) in a cohort of 80 SLE patients (76 female, 4 male), for most of whom serial samples spaning a three year period were available, as well as in 10 patients with biopsy proven primary Sjögren's syndrome (SS), 20 patients with rheumatoid arthritis, 10 patients with osteoarthritis and 20 normal control. Of the SLE patients, 60 were Caucasian, 10 were African American, 7 were Asian and 3 were others, including Native American. All individuals were found to have measurable clusterin in their serum. A caveat is, however, that the serum must be fresh or at most undergo only one freeze /thaw cycle, having been stored at −70° C., as clusterin or the epitope recognized by the mouse monoclonal anti-clusterin antibody is very unstable. Clusterin ranged in the serum of the SLE patients from 0.001 to 1.33 mg/ml, and in the normal controls from 0.12 to 0.94 mg/ml.

For the SLE patient group, mean clusterin levels were significantly lower than for normal controls (SLE 0.257±0.068 mg/ml; normal controls 0.415±0.125 mg/ml p=0.017). However, there was no difference in serum clusterin levels between the normal controls and RA (0.543±0.050 mg/ml), SS (0.570±0.062 mg/ml) or OA patients tested (0.590±0.062 mg/ml). We did not find any significant difference in the clusterin levels in males versus females within any of the disease groups or for the normal controls. The clusterin values that we report for the normal controls are slightly higher than those previously determined in humans (Hogasen, K. et al., *J. Immunol. Meth.* 160:107–115 (1993)), and likely reflect methodological differences.

For the SLE patients we found that there was a striking inverse correlation between the disease activity [SLAM-R (2)] and the levels of clusterin (FIG. 1). Thus, this suggests that the patients with higher disease activity had the lowest levels of clusterin. In individual patients where serial samples were available, spanning a three year time interval, the clusterin level tended to fall as the disease became more active. The disease features that correlated most strongly with the low levels of clusterin were the skin manifestations (FIG. 2A) (alopecia, p=0.002, skin ulcers <0.0001; skin rash p=0.23 and vasculitis p=0.097). The association of hair loss (alopecia) with low clusterin is consistent with the findings of Seigerg who showed that clusterin correlated with hair growth. Previous studies had shown that clusterin could be detected in $^{11}/_{15}$ skin lesions from SLE patients and in $^{5}/_{10}$ non affected skin biopsies, where, in the latter case, there was a much lower expression. Thus it is possible that the lower amounts of systemic clusterin reflects the consumption at the active sites.

To examine this issue further, we investigated the levels of circulating complement, which is generally used as a measure of complement consumption, a net result of activation. There was, however, no association found between the levels of circulating clusterin and serum C3 or C4 levels (C3, r=0.13, p=0.16; C4, r=0.15, p=0.13), indicating that consumption of clusterin in concert with the C3 and C4 was not the explanation for the low levels observed. For the autoantibodies tested, only for the IgG anti-cardiolipin antibodies was there a slight inverse correlation with clusterin levels (r=−0.17, p=0.08). Furthermore, the levels of anti-DNA, anti-Ro/SSA and anti-La/SSB autoantibodies did not correlate with the amounts of serum clusterin. Thus, the changes in the amount of serum clusterin, which occurred with disease activity, appeared to be independent of both complement (at least C3 and C4) and autoantibody levels with the exception of the anti-phospholipid, anti-cardiolipin autoantibodies. The later result is of interest given the lipid binding characteristics of clusterin.

Figure 2A:
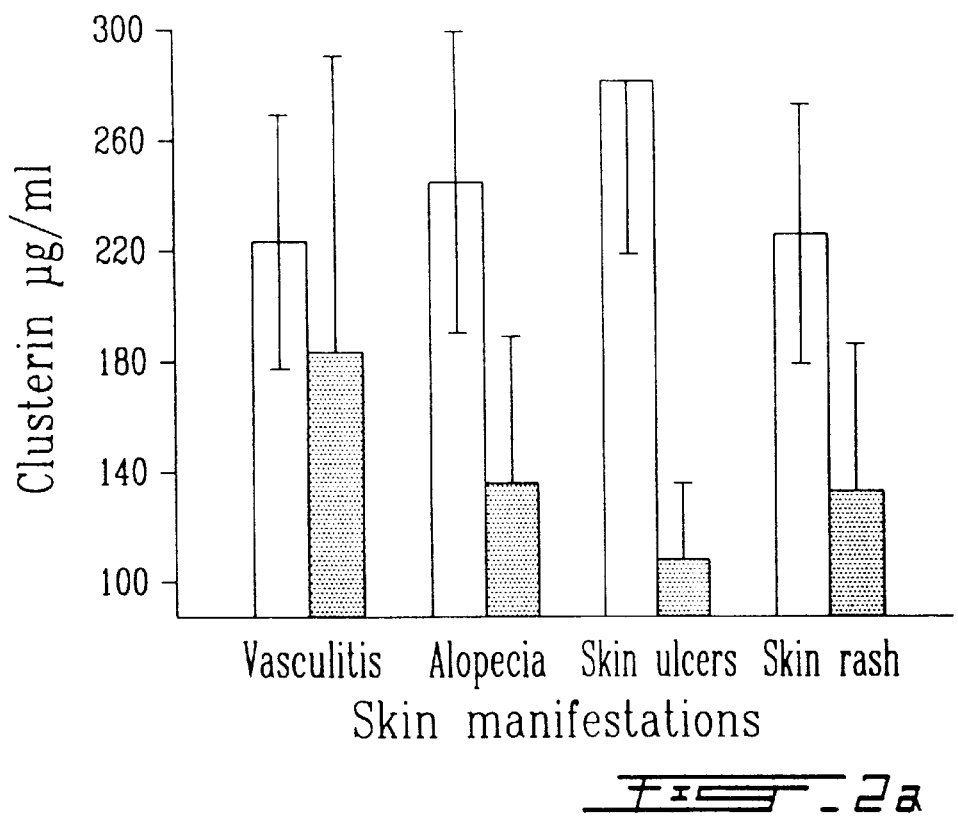
FIG. 2 illustrates mean serum clusterin levels (±95% confidence intervals) in SLE patients (a) ■ with and □ without disease features, related to skin manifestations, (b) with and without low peripheral blood cell counts, (c) □ with and ■ without arthritis, or an ■ abnormal hematocrit, (d) Mean serum clusterin levels (±SEM) in SLE patients with renal disease, abnormal serum creatinin, and protein or RBC in 24-hr urine samples.
Figure 2B:
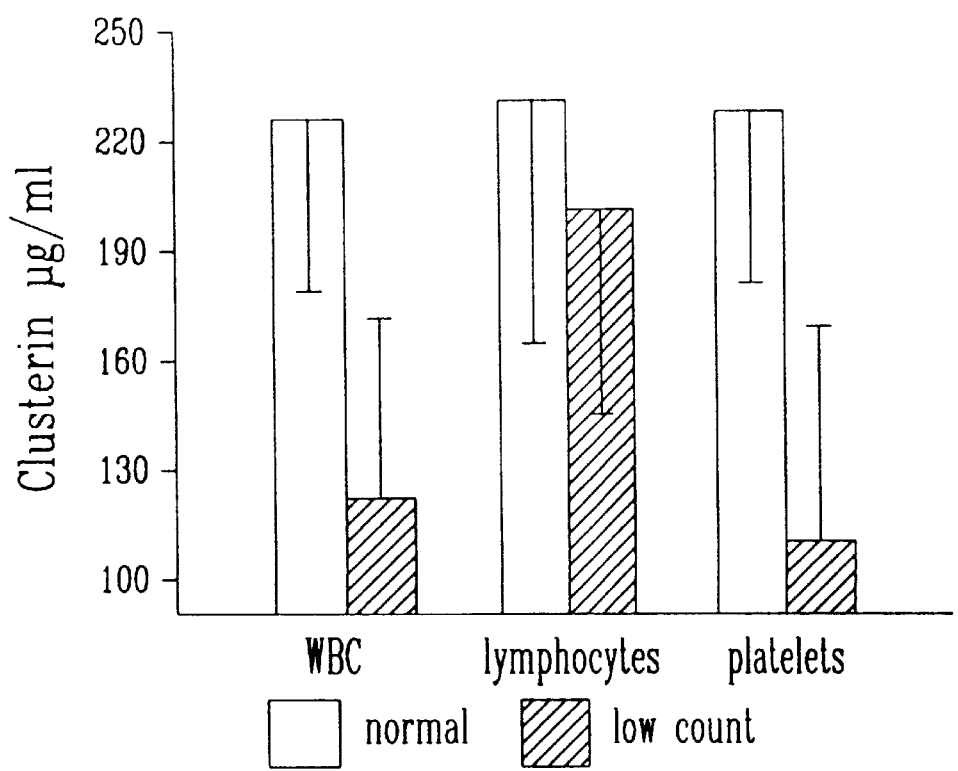
Figure 2C:
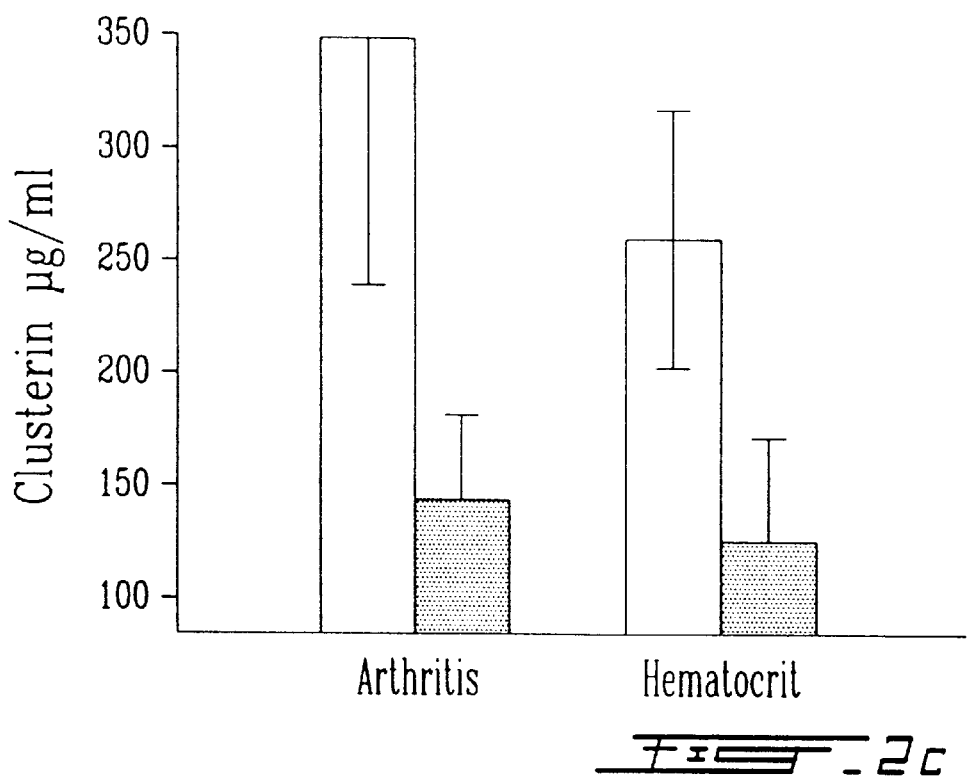

In contrast there was a significant association of low clusterin with low platelet and WBC counts (p=0.03, platelets; p=0.06 WBC) but not with low lymphocytes (FIG. 2B). This is of interest since platelets as well as polymorphonuclear leukocytes, but not lymphocytes, produce clusterin. Abnormal hematocrit values also correlated strongly with low clusterin levels (p<0.0001) (FIG. 2C); however, there was no significant linear correlation between the hematocrit value and the amount of clusterin. The presence of arthritis, a common feature of SLE (67% of individuals had arthritis), correlated strongly with low clusterin levels (FIG. 2C). Clusterin has previously been detected in the arthritic joints of patients with rheumatoid arthritis, but no studies have investigated its presence in the joints of patients with SLE.

As it has been shown that corticosteroids can suppress clusterin production, we investigated this as a possible explanation for the low levels of clusterin, since 50% of the patients in our cohort were receiving steroids. We did not find any significant correlation between clusterin levels and the amounts of steroids the patient received. The mean clusterin levels were 0.254±0.083 mg/ml (N=53) from the SLE patients not on steroids and 0.222±0.075 mg/ml (N=55) for those receiving steroid therapy.

Clusterin is a product of a gene located on human 8p21. The clusterin gene is polymorphic, with four of the seven alleles more common in African Americans, and rare in Caucasians. We found that the mean clusterin levels in the SLE patients were not significantly different among the different ethnic groups tested (Caucasians 0.26±0.075 mg/ml; African Americans 0.26±0.088 mg/ml; Asian 0.0.171±0.096 mg/ml; Other 0.463±0.25 mg/ml) . In our cohort, the group of African Americans is small and the genotypes of the individuals are as yet unknown. We cannot, as yet, rule out a contribution of a specific clusterin allele to the changes observed, although it appears likely that other regulatory factors that influence the levels of clusterin, may play important roles. To date, the SLE susceptibility alleles that have been mapped include the HLA DR3 and the C4 null locus, mannose binding lectin and the FcγRIIa, although it is likely that several other genes important in the etiology or pathogenesis will be found.

Figure 2D:
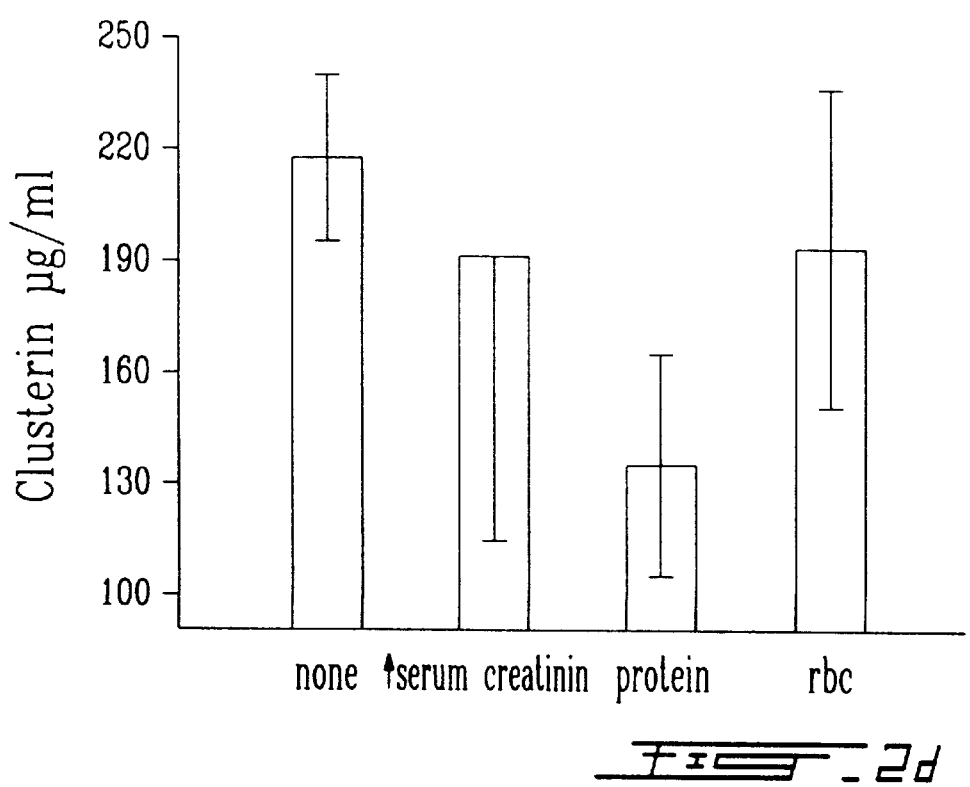

We also investigated the potential role of clusterin in the renal complications of SLE. We anticipated that there might be differences, since depletion of clusterin in plasma is associated with increased proteinuria in a Heymann nephritis model. Indeed, as seen in FIG. 2D, for the patients with protein in their 24 hour urine sample, the mean clusterin levels were significantly lower ($0.146 \pm 0.033$ mg clusterin/ml, compared to those with normal renal function $0.236 \pm 0.024$ mg clusterin/ml, $p=0.018$). However, although there was an inverse trend, the clusterin levels did not reach statistical significance for those with abnormal serum creatinin, but this may reflect the small number of patients with renal disease in our cohort (11 had abnormal serum creatinin). In membrane attack complexes (MAC) in the kidney, clusterin has been found to co-localize only with the Ig containing MAC. Folic acid has been shown to increase renal clusterin expression, although its impact on systemic clusterin levels is unknown. It is possible that folate supplement and/or tamoxifen, which has been shown to increase clusterin expression, could be used clinically. Similarly, methotrexate, which inhibits the action of the enzyme tetrahydrofolate reductase may block the effect of folate on renal clusterin expression.

The mechanisms that result in low systemic levels of clusterin, which occur with active disease in patients with SLE, are as yet unknown, but could involve genetic factors as well as environmental factors. Further studies are clearly warranted to examine in detail the changes in serum clusterin in the known animal models of SLE, in order to better understand the important role that this anti-inflammatory protein plays in this disease. It appears that the paucity of this protective protein in patients with SLE is apparently deleterious, and contributes to the inflammation, especially in the skin and joints.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A method to determine systemic lupus erythematosus (SLE) disease in a patient, which comprises the steps of:
    a) determining the amount of clusterin present in a serum, saliva or tissue sample of said patient with an anticlusterin antibody;
    b) comparing the amount of clusterin in step a) with normal serum, saliva or tissue sample, wherein a lower than normal amount is indicative of active systemic lupus erythematosus (SLE) disease.

2. A method according to claim 1, wherein said determining of clusterin amount present in a sample is effected by measuring said amount of clusterin weekly to monthly to follow disease activity, wherein a drop in said amount of clusterin is indicative of more active disease which necessitates more aggressive treatment.

* * * * *